(12) United States Patent
Mok

(10) Patent No.: US 11,648,422 B2
(45) Date of Patent: May 16, 2023

(54) APPARATUS AND METHODS OF GENERATING 4-DIMENSIONAL COMPUTER TOMOGRAPHY IMAGES

(71) Applicant: University of Macau, Macau (CN)

(72) Inventor: Greta S. P. Mok, Macau (CN)

(73) Assignee: University of Macau, Macau (CN)

( * ) Notice: Subject to any disclaimer, the term of this patent is extended or adjusted under 35 U.S.C. 154(b) by 534 days.

(21) Appl. No.: 16/596,817

(22) Filed: Oct. 9, 2019

(65) Prior Publication Data

US 2021/0106847 A1    Apr. 15, 2021

(51) Int. Cl.
*A61N 5/10* (2006.01)
*G06T 7/33* (2017.01)
*G06T 7/38* (2017.01)
*A61B 6/03* (2006.01)

(52) U.S. Cl.
CPC ............ *A61N 5/1071* (2013.01); *A61B 6/032* (2013.01); *A61B 6/037* (2013.01); *G06T 7/33* (2017.01); *G06T 7/38* (2017.01); *A61N 2005/1087* (2013.01); *G06T 2207/10081* (2013.01);
(Continued)

(58) Field of Classification Search
CPC .......... A61N 5/1071; A61N 2005/1087; A61B 6/032; A61B 6/037; G06T 7/33; G06T 7/38; G06T 2207/1008; G06T 2207/10104; G06T 2207/10108
See application file for complete search history.

(56) References Cited

U.S. PATENT DOCUMENTS

2010/0061607 A1* 3/2010 Sgouros .............. A61N 5/1039
                                                                        382/128
2019/0101655 A1* 4/2019 Wang .................... G01R 33/28

OTHER PUBLICATIONS

Fayad et al.; Generation of 4-dimensional CT images based on 4-dimensional PET-derived motion fields; published on Apr. 1, 2013; Journal of Nuclear Medicine Apr. 2013, 54 (4) pp. 631-638 (Year: 2013).*

(Continued)

*Primary Examiner* — Chao Sheng
(74) *Attorney, Agent, or Firm* — Spruson & Ferguson (Hong Kong) Limited

(57) ABSTRACT

The present disclosure provides a system comprising a SPECT or PET device; a CT device; and a computer comprising memory and a processor in communication with the memory, the memory comprising a computer application program for a method of performing dosimetric analysis of an organ. The computer application program is executable by the processor to perform the method. The method comprising receiving single photon emission computed tomography (SPECT) or positron emission tomography (PET) images at time instances, the SPECT or PET images relating to the organ. The method then receives a computed tomography (CT) image at one of the time instances, the CT image relating to the organ. Virtual CT images are then generated at the other time instances based on the received SPECT or PET images and the CT image. An absorbed dose of ionising radiation on the organ can then be measured based on the received SPECT or PET images, the received CT image, and the generated virtual CT images. The method generates the virtual CT images using any one of: SPECT to SPECT (or PET to PET) registration, CT to SPECT (PET) registration, and SPECT (PET) to CT registration.

15 Claims, 12 Drawing Sheets

(52) U.S. Cl.
CPC .............. *G06T 2207/10104* (2013.01); *G06T 2207/10108* (2013.01)

(56) References Cited

OTHER PUBLICATIONS

He B, Du Y, Song X, Segars WP, Frey EC. A Monte Carlo and physical phantom evaluation of quantitative In-111 SPECT. Phys Med Biol. 2005;50:4169-4185.

Li T, Ao ECI, Lambert B, Brans B, Vandenberghe S, Mok GSP. Quantitative imaging for targeted radionuclide therapy dosimetry-technical review. Theranostics. 2017;7:4551-4565.

Li T, Wu N-Y, Song N, Mok GSP. Evaluation of sequential SPECT and CT for targeted radionuclide therapy dosimetry. Ann Nucl Med. 2018;32:34-43.

He B, Frey EC. The impact of 3D volume of interest definition on accuracy and precision of activity estimation in quantitative SPECT and planar processing methods. Phys Med Biol 2010;55:3535-3544.

Mattsson S, Johansson L, Svegbom SL, et al. ICRP publication 128:radiation dose to patients from radiopharmaceuticals: a compendium of current information related to frequently used substances. Ann ICRP. 2015;44:7-321.

Huang B, Law MW-M, Khong P-L. Whole-body PET/CT scanning: estimation of radiation dose and cancer risk. Radiology 2009;251:166-174.

Sgouros G, Squeri S, Ballangrud _AM, et al. Patient-specific, 3-dimensional dosimetry in non-Hodgkin's lymphoma patients treated with 131I-anti-B1 antibody: assessment of tumor dose-response. J Nucl Med.2003;44:260-268.

Sgouros G, Kolbert KS, Sheikh A, et al. Patient-specific dosimetry for 131I thyroid cancer therapy using 124I PET and 3-dimensional-internal dosimetry (3D-ID) software. J Nucl Med. 2004;45:1366-1372.

Klein S, Staring M, Murphy K, Viergever MA, Pluim JP. Elastix: a toolbox for intensity-based medical image registration. IEEE Trans Med Imaging. 2010;29:196-205.

Studholme C, Hill DLG, Hawkes DJ. Automated three-dimensional registration of magnetic resonance and positron emission tomography brain images by multiresolution optimization of voxel similarity measures. Med Phys. 1997;24:25-35.

Rueckert D, Sonoda LI, Hayes C, Hill DL, Leach MO, Hawkes DJ. Nonrigid registration using free-form deformations: application to breast MR images. IEEE Trans Med Imaging. 1999;18:712-721.

Klein S, Pluim JP, Staring M, Viergever MA. Adaptive stochastic gradient descent optimisation for image registration. Int J Comput Vis. 2009;81:227-239.

Metz C, Klein S, Schaap M, van Walsum T, Niessen WJ. Nonrigid registration of dynamic medical imaging data using nD+ t B-splines and a groupwise optimization approach. Med Image Anal. 2011;15:238-249.

Segars W, Sturgeon G, Mendonca S, Grimes J, Tsui BM. 4D XCAT phantom for multimodality imaging research. Med Phys. 2010;37:4902-4915.

He B, Du Y, Segars WP, et al. Evaluation of quantitative imaging methods for organ activity and residence time estimation using a population of phantoms having realistic variations in anatomy and uptake. Med Phys. 2009;36:612-619.

Ao EC, Wu N-Y, Wang S-J, Song N, Mok GS. Improved dosimetry for targeted radionuclide therapy using nonrigid registration on sequential SPECT images. Med Phys. 2015;42:1060-1070.

Song N, He B, Frey E. The effect of volume-of-interest misregistration on quantitative planar activity and dose estimation. Phys Med Biol. 2010;55:5483-5497.

Frey EC, Tsui B. A practical projector-backprojector modeling attenuation, detector response, and scatter for accurate scatter compensation in SPECT. IEEE Trans Nucl Sci. 1993;40:1107-1116.

Frey EC, Tsui B. A new method for modeling the spatially-variant,object-dependent scatter response function in SPECT. IEEE Nucl Sci Symp. 1996;2:1082-1086.

Metz CE, Atkins F, Beck RN. The geometric transfer function component for scintillation camera collimators with straight parallel holes. Phys Med Biol. 1980;25:1059-1070.

Cheng L, Hobbs RF, Segars PW, Sgouros G, Frey EC. Improved dose-volume histogram estimates for radiopharmaceutical therapy by optimizing quantitative SPECT reconstruction parameters. Phys Med Biol. 2013;58:3631-3647.

Lanconelli N, Pacilio M, Meo SL, et al. A free database of radionuclide voxel S values for the dosimetry of nonuniform activity distributions. Phys Med Biol. 2012;57:517-533.

Silva EA, Panetta K, Agaian SS. Quantifying image similarity using measure of enhancement by entropy. Mobile Multimedia/Image Process Mil Sec Appl. 2007;6579:65790U.

Tanner C, Schnabel JA, Chung D, et al. Volume and shape preservation of enhancing lesions when applying non-rigid registration to a time series of contrast enhancing MR breast images. Paper presented at: International Conference on Medical Image Computing and Computer-Assisted Intervention; 2000.

Rohlfing T, Maurer CR, Bluemke DA, Jacobs MA. Volume-preserving nonrigid registration of MR breast images using free-form deformation with an incompressibility constraint. IEEE Trans Med Imaging. 2003;22:730-741.

Tiantian Li, Greta S. P. Mok. Virtual CT for reducing CT dose in targeted radionuclide therapy dosimetry. Med. Phys. 45 (11), Nov. 2018, 5138-5144.

\* cited by examiner

APPARATUS AND METHODS OF GENERATING 4-DIMENSIONAL COMPUTER TOMOGRAPHY IMAGES

TECHNICAL FIELD

The present invention relates generally to single photon emission computed tomography (SPECT)/computed tomography (CT) or positron emission tomography (PET)/CT scan to measure an absorbed dose of ionising radiation.

BACKGROUND

SPECT and PET scan have been proven to be accurate for activity quantification, making 3-dimensional (3D) dosimetry feasible for targeted radionuclide therapy (TRT). However, SPECT and PET images have relatively poor resolution, high noise levels, and insufficient anatomical information, leading to large uncertainties for image registration and segmentation.

SPECT and PET scan can be improved by using sequential CT images. However, CT-aided dosimetry requires good alignment between SPECT and CT images or PET and CT images at each time instance. A 1-voxel (<4.42 mm) misregistration between CT and SPECT images could result in quantitation errors as large as 6% for bone marrow.

Sequential CT images require multiple CT to be performed on a subject, which raises radiation concerns. For example, in serial (4-5) SPECT/CT scanning sessions of $^{111}$In-octreotide with 6 mCi injected doses for treatment planning, the effective dose from SPECT scan is 12.0 mSv[5], while the effective dose from a low dose CT scan (e.g., having voltage: 120 kV, current: 100-300 mA, pitch: 0.984, slice thickness: 0.625 mm, rotation time: 0.5 s) is 7 mSv[6]. The total effective dose of both SPECT and CT scans can be up to 47 mSv. Thus, in some cases, only a single CT scan is performed along with the serial SPECT scans for TRT dosimetry, with an effective dose of about 19 mSv.

There is a need to improve the SPECT/CT and PET/CT protocols for TRT.

SUMMARY

It is an object of the present invention to substantially overcome, or at least ameliorate, one or more disadvantages of existing arrangements.

Disclosed are arrangements to improve SPECT/CT or PET/CT scan for a dosimetric analysis. The present disclosure uses multiple SPECT/PET scans and one CT scan to generate multiple virtual CT images (i.e., 4-dimensional CT images). The virtual CT images can then be used to improve the SPECT/PET scan.

Aspects of the present disclosure provide that the generation of the 4-dimensional virtual CT images (i.e., a series of virtual CT images over time) is performed by determining motion vectors for registration between the single CT image and the SPECT/PET images and using the determined motion vectors to generate the virtual CT images.

Other aspects of the present disclosure provide that the generation of the virtual CT images is performed by determining motion vectors for registration between a SPECT/PET image corresponding to the single CT image and the remaining SPECT/PET images and using the determined motion vectors to generate the virtual CT images.

According to a first aspect of the present disclosure, there is provided a system comprising: a SPECT or PET device; a CT device; and a computer comprising memory and a processor in communication with the memory, the memory comprising a computer application program for a method of performing dosimetric analysis of an organ, wherein the computer application program is executable by the processor to perform the method, the method comprising: receiving single photon emission computed tomography (SPECT) or positron emission tomography (PET) images at time instances, the SPECT or PET images relating to the organ; receiving a computed tomography (CT) image at one of the time instances, the CT image relating to the organ; generate virtual CT images at the other time instances based on the received SPECT or PET images and the CT image; and measure an absorbed dose of ionising radiation on the organ based on the received SPECT or PET images, the received CT image, and the generated virtual CT images.

According to a second aspect of the present disclosure, there is provided a non-transitory computer readable medium comprising a computer application program for a method of performing dosimetric analysis of an organ, the method comprising: receiving single photon emission computed tomography (SPECT) or positron emission tomography (PET) images at time instances, the SPECT or PET images relating to the organ; receiving a computed tomography (CT) image at one of the time instances, the CT image relating to the organ; generate virtual CT images at the other time instances based on the received SPECT or PET images and the CT image; and measure an absorbed dose of ionising radiation on the organ based on the received SPECT or PET images, the received CT image, and the generated virtual CT images.

According to a third aspect of the present disclosure, there is provided a computer-implemented method of performing dosimetric analysis, the method comprising: receiving single photon emission computed tomography (SPECT) or positron emission tomography (PET) images at time instances, the SPECT or PET images relating to an organ; receiving a computed tomography (CT) image at one of the time instances, the CT image relating to the organ; generate virtual CT images at the other time instances based on the received SPECT or PET images and the CT image; and measure an absorbed dose of ionising radiation on the organ based on the received SPECT or PET images, the received CT image, and the generated virtual CT images.

Other aspects are also disclosed.

BRIEF DESCRIPTION OF THE DRAWINGS

At least one embodiment of the present invention will now be described with reference to the drawings and appendices, in which.

DETAILED DESCRIPTION INCLUDING BEST MODE

Figure 1:
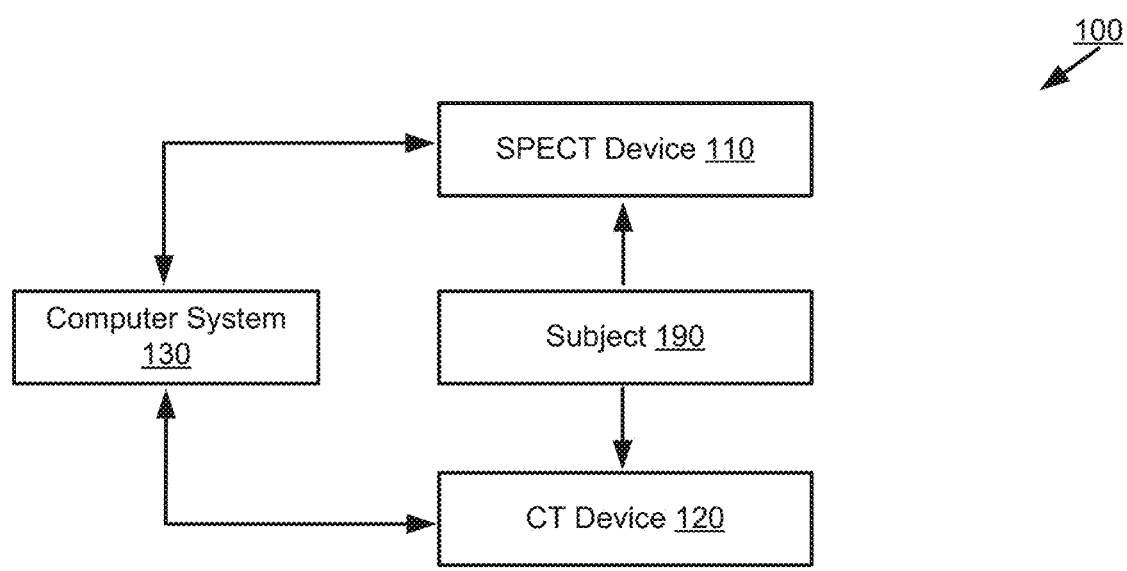
FIG. 1 shows a system for performing SPECT/CT scan in accordance with aspects of the present disclosure.

Where reference is made in any one or more of the accompanying drawings to steps and/or features, which have the same reference numerals, those steps and/or features have for the purposes of this description the same function(s) or operation(s), unless the contrary intention appears.

FIG. 1 shows a system 100 for performing the SPECT/CT scan. The system 100 includes a SPECT device 110, a CT device 120, and a computer system 130. The system 100 is used to acquire SPECT images (using the SPECT device 110) and CT images (using the CT device 120) of an organ of a subject 190.

In an alternative arrangement, a PET device is used instead of a SPECT device to perform PET/CT protocol. Hereinafter, for convenience sake, the present disclosure will only describe the use of the SPECT device 110 to acquire SPECT images and use the acquired SPECT images to generate the 4-dimensional CT images. However, it should be understood that the SPECT device 110 can be replaced by a PET device to acquire PET images. The acquired PET images can then be used rather than the SPECT images described below.

The SPECT device 110 includes a gamma camera (not shown) to capture a gamma-emitting radioisotope (a radionuclide) that is inserted into the subject 190. The SPECT device 110 then captures SPECT images of an organ of the subject 190. The SPECT images are then forwarded to the computer system 130.

The CT device 120 includes an X-ray generator (not shown) and an X-ray detector (not shown) to perform X-ray measurements of an organ of the subject 190. The X-ray measurements are then transmitted to the computer system 130, which processes the X-ray measurements to produce CT images.

In one arrangement, the SPECT device 110 and the CT device 120 may be integrated into one device.

The subject 190 can be a person or an animal. The SPECT device 110 and the CT device 120 can take images of an organ (e.g., brain, lungs, heart, etc.) of the subject 190.

Computer System 130

Figure 2A:
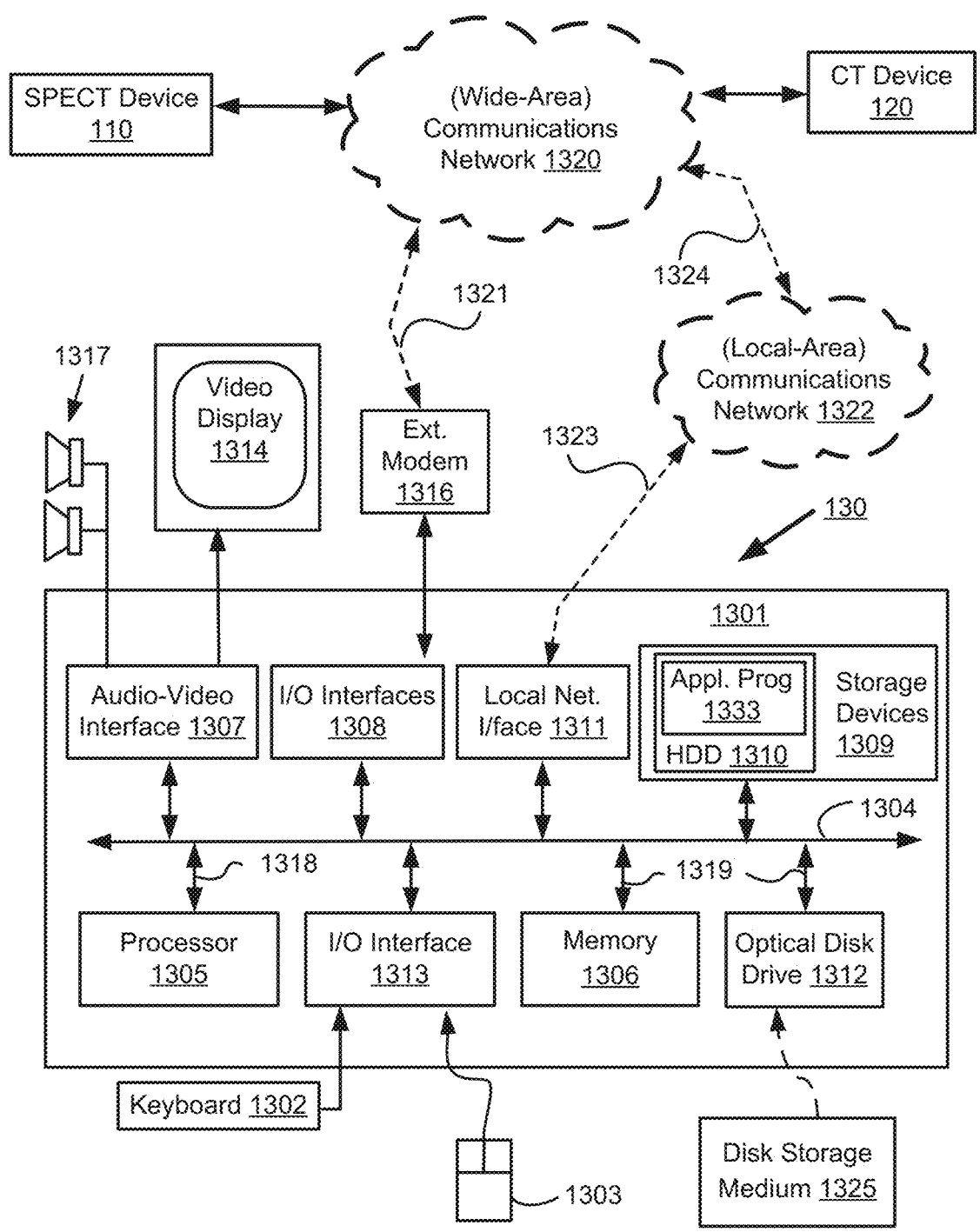
FIGS. 2A and 2B form a schematic block diagram of a general purpose computer system upon which arrangements described can be practiced.
Figure 2B:
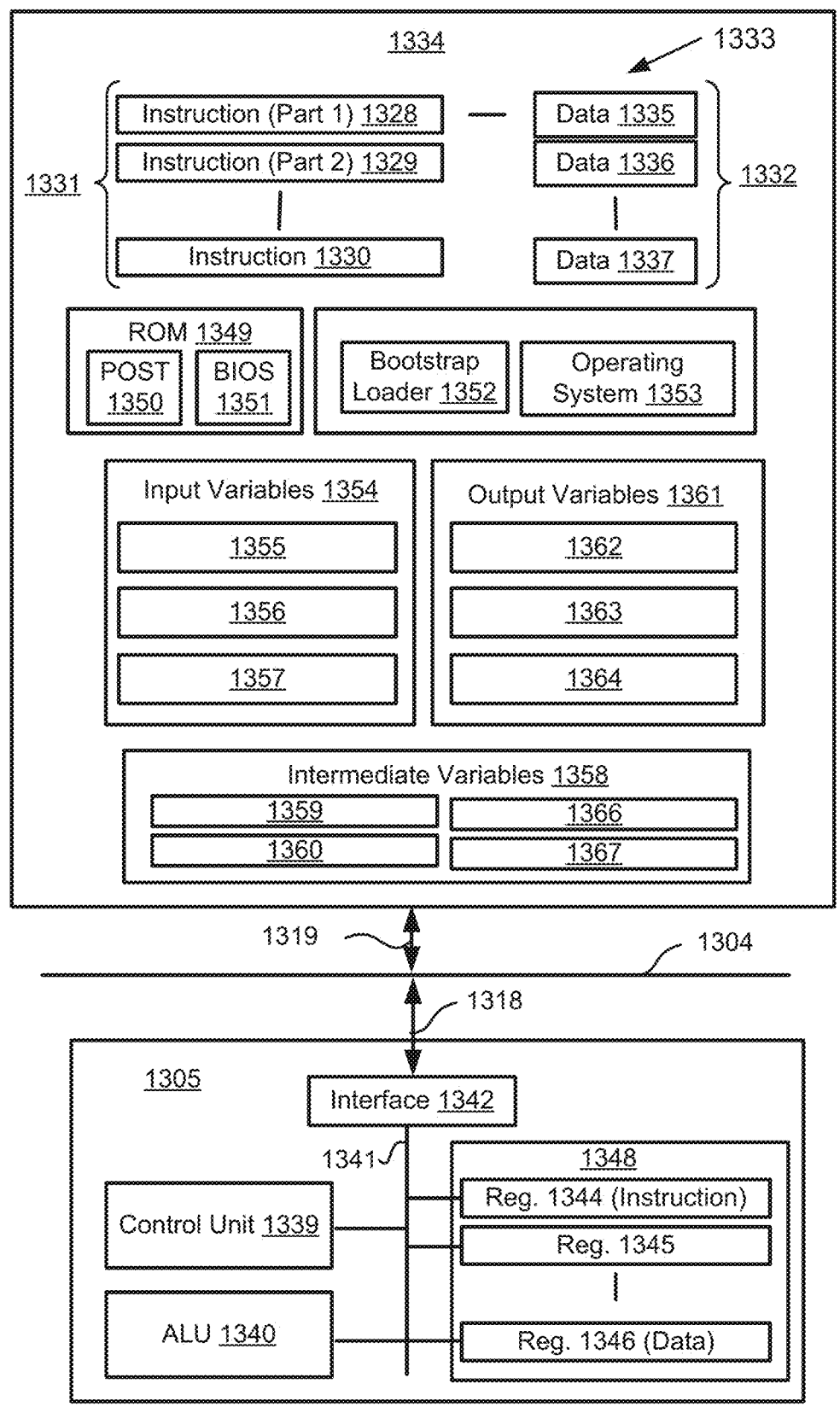

FIGS. 2A and 2B depict a general-purpose computer system 130, upon which the various arrangements described can be practiced.

As seen in FIG. 2A, the computer system 130 includes: a computer module 1301; input devices such as a keyboard 1302 and a mouse pointer device 1303; and output devices including a display device 1314 and loudspeakers 1317. An external Modulator-Demodulator (Modem) transceiver device 1316 may be used by the computer module 1301 for communicating to and from a communications network 1320 via a connection 1321. The communications network 1320 may be a wide-area network (WAN), such as the Internet, a cellular telecommunications network, or a private WAN. Where the connection 1321 is a telephone line, the modem 1316 may be a traditional "dial-up" modem. Alternatively, where the connection 1321 is a high capacity (e.g., cable) connection, the modem 1316 may be a broadband modem. A wireless modem may also be used for wireless connection to the communications network 1320.

The computer module 1301 typically includes at least one processor unit 1305, and a memory unit 1306. For example, the memory unit 1306 may have semiconductor random access memory (RAM) and semiconductor read only memory (ROM). The computer module 1301 also includes an number of input/output (I/O) interfaces including: an audio-video interface 1307 that couples to the video display 1314 and loudspeakers 1317; an I/O interface 1313 that couples to the keyboard 1302, mouse 1303, and optionally a joystick or other human interface device (not illustrated); and an interface 1308 for the external modem 1316. In some implementations, the modem 1316 may be incorporated within the computer module 1301, for example within the interface 1308. The computer module 1301 also has a local network interface 1311, which permits coupling of the computer system 130 via a connection 1323 to a local-area communications network 1322, known as a Local Area Network (LAN). As illustrated in FIG. 2A, the local communications network 1322 may also couple to the wide network 1320 via a connection 1324, which would typically include a so-called "firewall" device or device of similar functionality. The local network interface 1311 may comprise an Ethernet circuit card, a Bluetooth® wireless arrangement or an IEEE 802.11 wireless arrangement; however, numerous other types of interfaces may be practiced for the interface 1311.

The I/O interfaces 1308 and 1313 may afford either or both of serial and parallel connectivity, the former typically being implemented according to the Universal Serial Bus (USB) standards and having corresponding USB connectors (not illustrated). Storage devices 1309 are provided and typically include a hard disk drive (HDD) 1310. Other storage devices such as a floppy disk drive and a magnetic tape drive (not illustrated) may also be used. An optical disk drive 1312 is typically provided to act as a non-volatile source of data. Portable memory devices, such optical disks (e.g., CD-ROM, DVD, Blu-ray Disc™), USB-RAM, portable, external hard drives, and floppy disks, for example, may be used as appropriate sources of data to the system 130.

As shown in FIG. 2A, the SPECT device 110 and the CT device 120 are connected to the WAN 1320. In an alternative arrangement, the SPECT device 110 and the CT device 120 can be connected to the LAN 1322 or the I/O Interfaces 1308 to communicate with the computer system 130.

The components 1305 to 1313 of the computer module 1301 typically communicate via an interconnected bus 1304 and in a manner that results in a conventional mode of operation of the computer system 130 known to those in the relevant art. For example, the processor 1305 is coupled to the system bus 1304 using a connection 1318. Likewise, the memory 1306 and optical disk drive 1312 are coupled to the system bus 1304 by connections 1319. Examples of computers on which the described arrangements can be practised include IBM-PC's and compatibles, Sun Sparcstations, Apple Mac™ or like computer systems.

Figure 3:
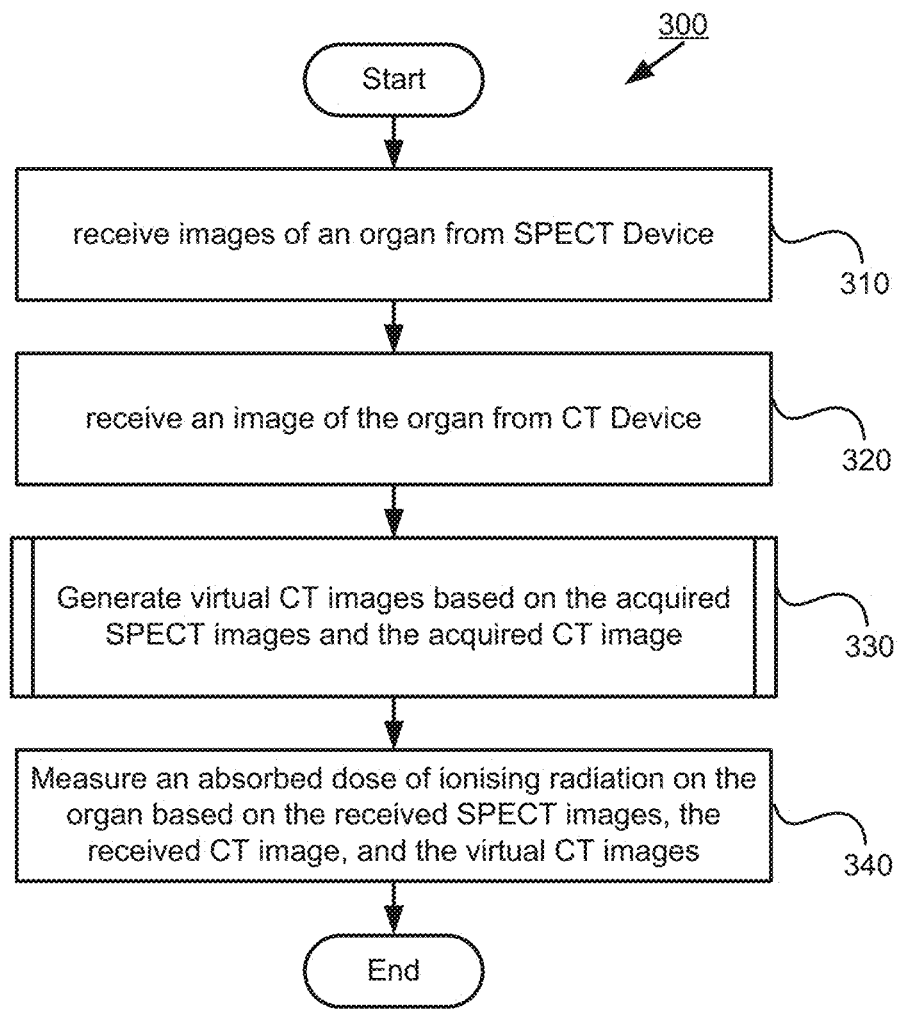
FIG. 3 is a flow chart of a method of measuring an absorbed dose of ionising radiation in accordance with aspects of the present disclosure.

The method and sub-processes for dosimetric analysis and generating virtual CT images may be implemented using the computer system 130 wherein the processes of Figs. FIG. 3 and sub-processes of FIGS. 4A to 6B to be described, may be implemented as one or more software application programs 1333 executable within the computer system 130. In particular, the steps of the method of FIG. 3 and sub-processes of FIGS. 4A to 6B are effected by instructions 1331 (see FIG. 2B) in the software 1333 that are carried out within the computer system 130. The software instructions 1331 may be formed as one or more code modules, each for performing one or more particular tasks. The software may also be divided into two separate parts, in which a first part and the corresponding code modules performs the dosimetric analysis and virtual CT image generation methods and a second part and the corresponding code modules manage a user interface between the first part and the user.

The software may be stored in a computer readable medium, including the storage devices described below, for example. The software is loaded into the computer system 130 from the computer readable medium, and then executed by the computer system 130. A computer readable medium having such software or computer program recorded on the computer readable medium is a computer program product. The use of the computer program product in the computer system 130 preferably effects an advantageous apparatus for performing dosimetric analysis and generating virtual CT images.

The software 1333 is typically stored in the HDD 1310 or the memory 1306. The software is loaded into the computer system 130 from a computer readable medium, and executed by the computer system 130. Thus, for example, the software 1333 may be stored on an optically readable disk storage medium (e.g., CD-ROM) 1325 that is read by the optical disk drive 1312. A computer readable medium having such software or computer program recorded on it is a computer program product. The use of the computer program product in the computer system 130 preferably effects an apparatus for performing dosimetric analysis and generating virtual CT images.

In some instances, the application programs 1333 may be supplied to the user encoded on one or more CD-ROMs 1325 and read via the corresponding drive 1312, or alternatively may be read by the user from the networks 1320 or 1322. Still further, the software can also be loaded into the computer system 130 from other computer readable media. Computer readable storage media refers to any non-transitory tangible storage medium that provides recorded instructions and/or data to the computer system 130 for execution and/or processing. Examples of such storage media include floppy disks, magnetic tape, CD-ROM, DVD, Blu-ray™ Disc, a hard disk drive, a ROM or integrated circuit, USB memory, a magneto-optical disk, or a computer readable card such as a PCMCIA card and the like, whether or not such devices are internal or external of the computer module 1301. Examples of transitory or non-tangible computer readable transmission media that may also participate in the provision of software, application programs, instructions and/or data to the computer module 1301 include radio or infra-red transmission channels as well as a network connection to another computer or networked device, and the Internet or Intranets including e-mail transmissions and information recorded on Websites and the like.

The second part of the application programs 1333 and the corresponding code modules mentioned above may be executed to implement one or more graphical user interfaces (GUIs) to be rendered or otherwise represented upon the display 1314. Through manipulation of typically the keyboard 1302 and the mouse 1303, a user of the computer system 130 and the application may manipulate the interface in a functionally adaptable manner to provide controlling commands and/or input to the applications associated with the GUI(s). Other forms of functionally adaptable user interfaces may also be implemented, such as an audio interface utilizing speech prompts output via the loudspeakers 1317 and user voice commands input via a microphone.

FIG. 2B is a detailed schematic block diagram of the processor 1305 and a "memory" 1334. The memory 1334 represents a logical aggregation of all the memory modules (including the HDD 1309 and semiconductor memory 1306) that can be accessed by the computer module 1301 in FIG. 2A.

When the computer module 1301 is initially powered up, a power-on self-test (POST) program 1350 executes. The POST program 1350 is typically stored in a ROM 1349 of the semiconductor memory 1306 of FIG. 2A. A hardware device such as the ROM 1349 storing software is sometimes referred to as firmware. The POST program 1350 examines hardware within the computer module 1301 to ensure proper functioning and typically checks the processor 1305, the memory 1334 (1309, 1306), and a basic input-output systems software (BIOS) module 1351, also typically stored in the ROM 1349, for correct operation. Once the POST program 1350 has run successfully, the BIOS 1351 activates the hard disk drive 1310 of FIG. 2A. Activation of the hard disk drive 1310 causes a bootstrap loader program 1352 that is resident on the hard disk drive 1310 to execute via the processor 1305. This loads an operating system 1353 into the RAM memory 1306, upon which the operating system 1353 commences operation. The operating system 1353 is a system level application, executable by the processor 1305, to fulfil various high level functions, including processor management, memory management, device management, storage management, software application interface, and generic user interface.

The operating system 1353 manages the memory 1334 (1309, 1306) to ensure that each process or application running on the computer module 1301 has sufficient memory in which to execute without colliding with memory allocated to another process. Furthermore, the different types of memory available in the system 130 of FIG. 2A must be used properly so that each process can run effectively. Accordingly, the aggregated memory 1334 is not intended to illustrate how particular segments of memory are allocated (unless otherwise stated), but rather to provide a general view of the memory accessible by the computer system 130 and how such is used.

As shown in FIG. 2B, the processor 1305 includes a number of functional modules including a control unit 1339, an arithmetic logic unit (ALU) 1340, and a local or internal memory 1348, sometimes called a cache memory. The cache memory 1348 typically includes a number of storage registers 1344-1346 in a register section. One or more internal busses 1341 functionally interconnect these functional modules. The processor 1305 typically also has one or more interfaces 1342 for communicating with external devices via the system bus 1304, using a connection 1318. The memory 1334 is coupled to the bus 1304 using a connection 1319.

The application program 1333 includes a sequence of instructions 1331 that may include conditional branch and loop instructions. The program 1333 may also include data 1332 which is used in execution of the program 1333. The instructions 1331 and the data 1332 are stored in memory locations 1328, 1329, 1330 and 1335, 1336, 1337, respectively. Depending upon the relative size of the instructions 1331 and the memory locations 1328-1330, a particular instruction may be stored in a single memory location as depicted by the instruction shown in the memory location 1330. Alternately, an instruction may be segmented into a number of parts each of which is stored in a separate memory location, as depicted by the instruction segments shown in the memory locations 1328 and 1329.

In general, the processor 1305 is given a set of instructions which are executed therein. The processor 1305 waits for a subsequent input, to which the processor 1305 reacts to by executing another set of instructions. Each input may be provided from one or more of a number of sources, including data generated by one or more of the input devices 1302, 1303, data received from an external source across one of the networks 1320, 1302, data retrieved from one of the storage devices 1306, 1309 or data retrieved from a storage medium 1325 inserted into the corresponding reader 1312, all depicted in FIG. 2A. The execution of a set of the instructions may in some cases result in output of data. Execution may also involve storing data or variables to the memory 1334.

The disclosed dosimetric analysis and virtual CT image generation arrangements use input variables 1354, which are stored in the memory 1334 in corresponding memory locations 1355, 1356, 1357. The dosimetric analysis and virtual CT image generation arrangements produce output variables 1361, which are stored in the memory 1334 in corresponding memory locations 1362, 1363, 1364. Intermediate variables 1358 may be stored in memory locations 1359, 1360, 1366 and 1367.

Referring to the processor 1305 of FIG. 2B, the registers 1344, 1345, 1346, the arithmetic logic unit (ALU) 1340, and the control unit 1339 work together to perform sequences of micro-operations needed to perform "fetch, decode, and execute" cycles for every instruction in the instruction set making up the program 1333. Each fetch, decode, and execute cycle comprises:

a fetch operation, which fetches or reads an instruction 1331 from a memory location 1328, 1329, 1330;

a decode operation in which the control unit 1339 determines which instruction has been fetched; and an execute operation in which the control unit 1339 and/or the ALU 1340 execute the instruction.

Thereafter, a further fetch, decode, and execute cycle for the next instruction may be executed. Similarly, a store cycle may be performed by which the control unit 1339 stores or writes a value to a memory location 1332.

Each step or sub-process in the processes of FIGS. 3 to 6B is associated with one or more segments of the program 1333 and is performed by the register section 1344, 1345, 1347, the ALU 1340, and the control unit 1339 in the processor 1305 working together to perform the fetch, decode, and execute cycles for every instruction in the instruction set for the noted segments of the program 1333.

The method of performing dosimetric analysis and virtual CT image generation may alternatively be implemented in dedicated hardware such as one or more integrated circuits performing the functions or sub functions of the method and sub-processes of FIGS. 3 to 6B. Such dedicated hardware may include graphic processors, digital signal processors, or one or more microprocessors and associated memories.

Dosimetric Analysis Method 300

FIG. 3 shows a method 300 for performing a dosimetric analysis. The method 300 can be implemented as one or more software application programs 1333 executable within the computer system 130.

The method 300 commences with step 310 by receiving SPECT images from the SPECT device 110. The SPECT device 110 acquires the SPECT images of an organ of the subject 190 at different time instances. The method 300 proceeds from step 310 to step 320.

In step 320, the CT device 120 and the computer system 130 operate to produce a CT image of the organ (which is the same organ of step 310). The CT image is captured at one of the time instances at which the SPECT images are captured. The method 300 proceeds from step 320 to sub-process 330.

Sub-process 330 generates virtual CT images based on the acquired SPECT images (step 310) and the acquired CT image (step 320). The generated virtual CT images are at the time instances at which the SPECT images are captured. Three implementations of the sub-process 330 are described respectively in FIGS. 4A, 5A, and 6A, which will be described hereinafter. The method 300 proceeds from sub-process 330 to step 340.

In step 340, the method 300 measures an absorbed dose of ionising radiation on the organ based on the acquired SPECT images, the acquired CT image, and the virtual CT images. The acquired CT image and the virtual CT images are first used for attenuation and scatter correction for the corresponding SPECT images. The organ is segmented out on the CT image and the virtual CT images and then used to map out the corresponding organ on SPECT images (acquired at step 310). The segmented images are then used to determine the activity of the target organ at different time instances. In particular, the segmented images are curve fitted to estimate the time activity curve and the cumulative activity, which is then convolved to a dose kernel to calculate the absorbed dose of the organs. The method 300 concludes at the conclusion of step 340.

Sub-Process 330A

Figure 4A:
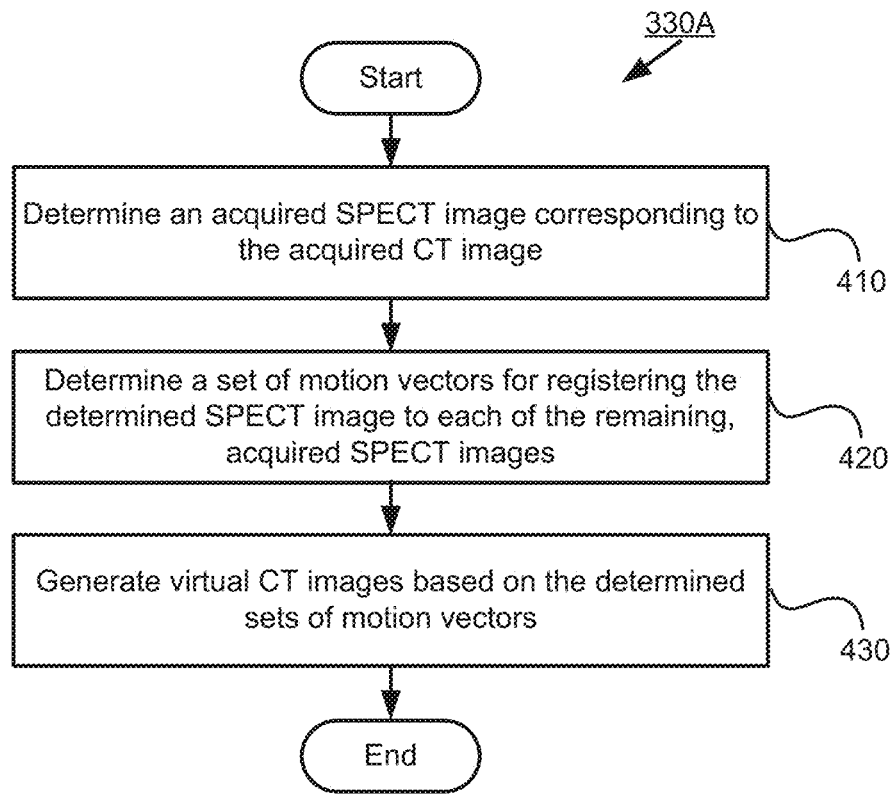
FIG. 4A is a flow chart of a sub-process of generating virtual CT images for the method of FIG. 3.
Figure 4B:
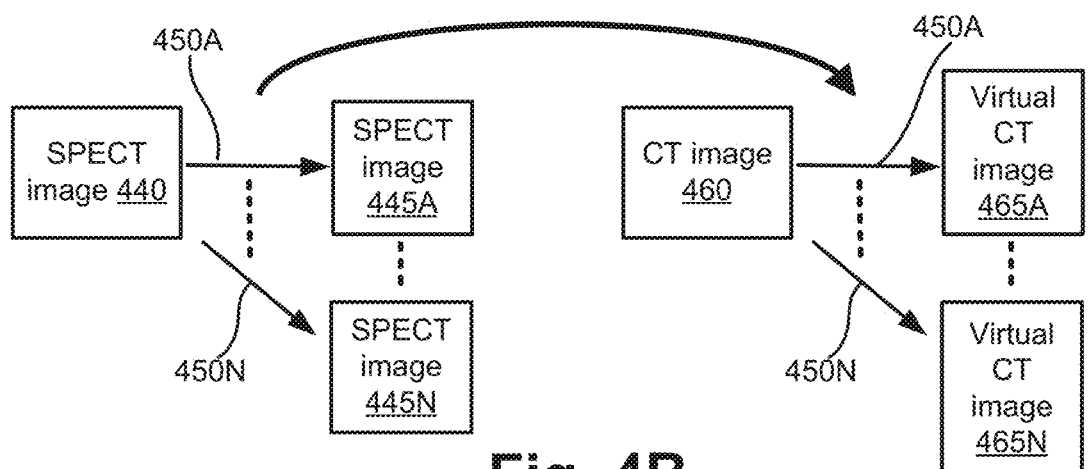
FIG. 4B illustrates the sub-process of FIG. 4A.

FIGS. 4A and 4B show the first implementation of the sub-process 330. Hereinafter, the first implementation of sub-process 330 will be referred to as sub-process 330A for convenience sake. FIG. 4A shows a flow chart of sub-process 330A, while FIG. 4B shows an illustration of the sub-process 330A.

FIG. 4B shows a CT image 460 (acquired at step 320), SPECT images 445A to 445N and 440 (acquired at step 310) captured at N+1 time instances, and virtual CT images 465A to 465N at N time instances. The number of time instances used is for ease of explanation only.

Sub-process 330A commences at step 410 by determining which one of the SPECT images (captured at step 310) correspond with the acquired CT image (step 320). The determination is performed by comparing the time instances at which the SPECT images 445A to 445N and 440 and the CT image 460 are captured. The SPECT image 440 having the same time instance as the CT image 460 is the SPECT image determined to correspond with the acquired CT image 460.

FIG. 4B shows the SPECT image 440 as the SPECT image corresponding with the acquired CT image 460 (i.e., the SPECT image 440 is captured at the same time instance as the CT image 460). The remaining SPECT images 445A to 445N are the SPECT images captured at the remaining N time instances. The SPECT images 445A to 445N and 440 are compensated with geometric collimator-detector response (GCDR) without attenuation correction (AC) and scatter correction (SC).

Sub-process 330A proceeds from step 410 to step 420.

In step 420, sub-process 330 determines a set of motion vectors (e.g., 450A) for registering the determined SPECT image 440 to each of the remaining, acquired SPECT images 445A to 445N. Therefore, the SPECT image 440 is the moving image and the SPECT images 445A to 445N are the fixed images. Each of the motion vectors 450A to 450N is a vector describing the transformation of each pixel of the SPECT image 440 in order to register the SPECT image 440 to the other SPECT images 445A to 445N. The transformation may include linear transformations (including rotation, scaling, translation, and other affine transforms) and non-rigid transformations (including radial basis functions, physical continuum models, and large deformation models). Therefore, the set of motion vectors 450A provides the transformation required to register the SPECT image 440 to the SPECT image 445A at a first time instance. Similarly, the set of motion vectors 450B provides the transformation required to register the SPECT image 440 to the SPECT image 445B at a second time instance.

Sub-process 330A proceeds from step 420 to step 430.

In step 430, virtual CT images 465A to 465N are generated based on the determined sets of motion vectors 450A to 450N. To generate a virtual CT image 465A at a first time instance (which is the same time instance as SPECT image 445A), the CT image 460 is transformed using the set of motion vectors 450A. Accordingly, the respective virtual CT images 465A to 465N are generated at N time instances corresponding with the N time instances at which the SPECT images 445A to 445N are captured.

In one arrangement, the motion vectors 450A to 450N relate to affine plus B-spline non-rigid image registration method. To perform the non-rigid registration, mutual information is normalised for 20000 pixels which are randomly selected for each resolution, and a three-level, multi-resolution approach with different grid sizes (8×8×8, 4×4×4, 1×1×1) is used to speed up both affine and B-spline registrations. For B-spline registrations, a bending energy term regularizes the deformation field to keep the rigidity and avoid the folding of local features. A stochastic gradient descent algorithm with 1000 iterations is used to iteratively solve the registration problem with adaptive step size prediction.

Therefore, by applying each set of motion vectors 450A to 450N, virtual CT images 465A to 465N are generated at N time instances.

Sub-process 330A concludes at the conclusion of step 430.

Sub-Process 330B

Figure 5A:
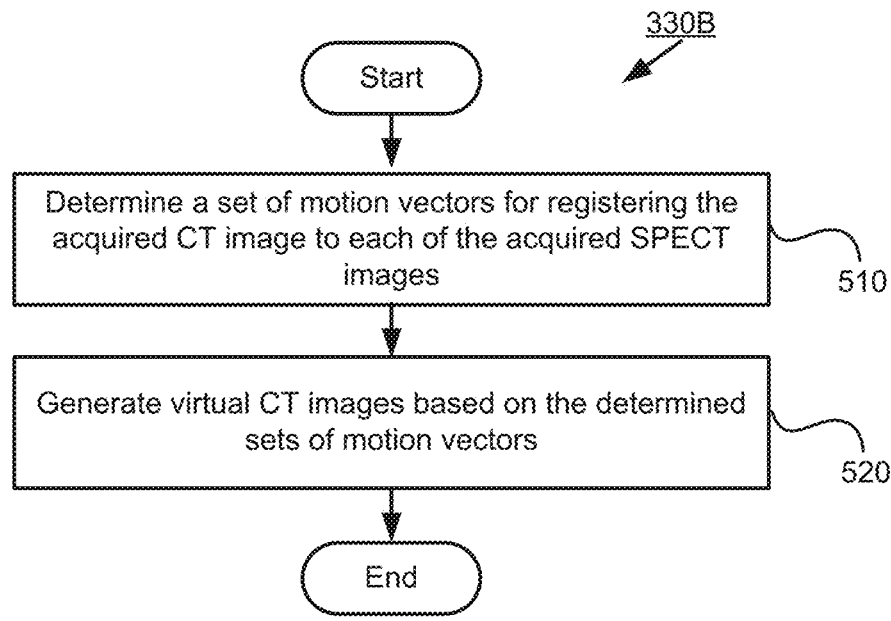
FIG. 5A is a flow chart of an alternative sub-process of generating virtual CT images for the method of FIG. 3.
Figure 5B:
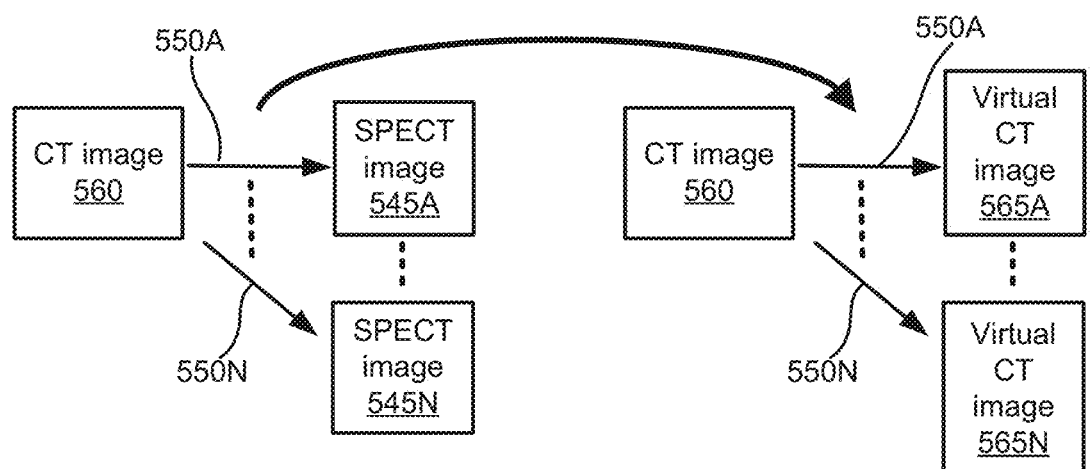
FIG. 5B illustrates the sub-process of FIG. 5A.

FIGS. 5A and 5B show the second implementation of the sub-process 330. Hereinafter, the second implementation of sub-process 330 will be referred to as sub-process 330B for convenience sake. FIG. 5A shows a flow chart of sub-process 330B, while FIG. 5B shows an illustration of the sub-process 330B.

FIG. 5B shows a CT image 560 (acquired at step 320), SPECT images 545A to 545N (acquired at step 310) captured at N time instances, and virtual CT images 565A to 565N. The number of time instances used is for ease of explanation only.

Sub-process 330B commences at step 510 by determining a set of motion vectors (e.g., 550A) for registering the acquired CT image 560 (at step 320) to each of the acquired SPECT images 545A to 545N. The registration between the CT image 560 and a SPECT image at the same time instance is not required. Therefore, the SPECT images 545A to 545N do not include the SPECT image captured at the same time instance as the CT image 560. The SPECT images 545A to 545N are compensated with geometric collimator-detector response (GCDR) without AC and SC.

Therefore, in sub-process 330B, the CT image 560 is the moving image and the SPECT images 545A to 545N are the fixed images. Each of the motion vectors 550A to 550N is a vector describing the transformation of each pixel of the CT image 560 in order to register the CT image 560 to the SPECT images 545A to 545N. The transformation may include linear transformations (including rotation, scaling, translation, and other affine transforms) and non-rigid transformations (including radial basis functions, physical continuum models, and large deformation models). Therefore, the set of motion vectors 550A provides the transformation required to register the CT image 560 to the SPECT image 545A at a first time instance. Similarly, the set of motion vectors 550B provides the transformation required to register the CT image 560 to the SPECT image 545B at a second time instance.

Sub-process 330B proceeds from step 510 to step 520.

In step 520, virtual CT images 565A to 565N are generated based on the determined sets of motion vectors 550A to 550N. To generate a virtual CT image 565A at a first time instance (which is the same time instance as SPECT image 545A), the CT image 560 is transformed using the set of motion vectors 550A. Accordingly, the respective virtual CT images 565A to 565N are generated at N time instances corresponding with the N time instances at which the SPECT images 545A to 545N are captured.

In one arrangement, the motion vectors 550A to 550N relate to affine plus B-spline non-rigid image registration method. To perform the non-rigid registration, mutual information is normalised for 20000 pixels which are randomly selected for each resolution, and a three-level, multi-resolution approach with different grid sizes (8×8×8, 4×4×4, 1×1×1) is used to speed up both affine and B-spline registrations. For B-spline registrations, a bending energy term regularizes the deformation field to keep the rigidity and avoid the folding of local features. A stochastic gradient descent algorithm with 1000 iterations is used to iteratively solve the registration problem with adaptive step size prediction.

Therefore, by applying each set of motion vectors 550A to 550N, virtual CT images 565A to 565N are generated. Each of the virtual CT images 565A to 565N corresponds to the time instance at which the respective SPECT images 545A to 545N are captured.

Sub-process 330B concludes at the conclusion of step 520.

Sub-Process 330C

Figure 6A:
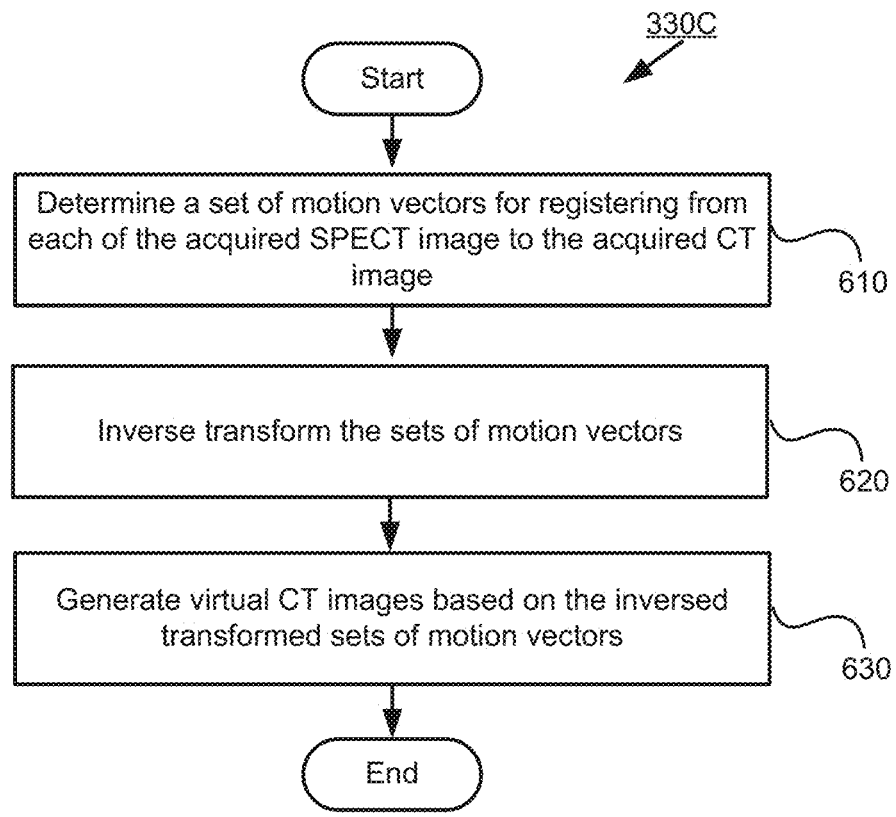
FIG. 6A is a flow chart of another alternative sub-process of generating virtual CT images for the method of FIG. 3.
Figure 6B:
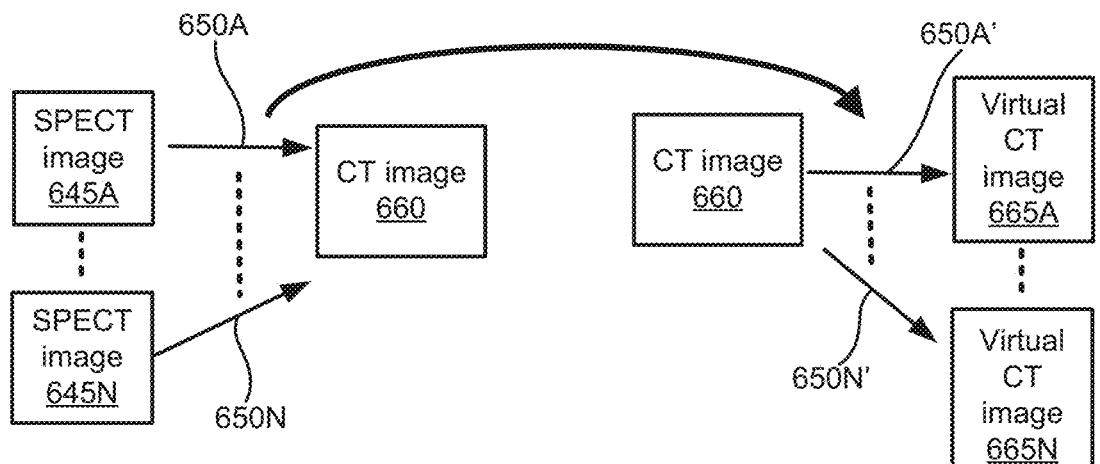
FIG. 6B illustrates the sub-process of FIG. 6A.

FIGS. 6A and 6B show the third implementation of the sub-process 330. Hereinafter, the third implementation of sub-process 330 will be referred to as sub-process 330C for convenience sake. FIG. 6A shows a flow chart of sub-process 330C, while FIG. 6B shows an illustration of the sub-process 330C.

FIG. 6B shows a CT image 660 (acquired at step 320), SPECT images 645A to 645N (acquired at step 310) captured at N time instances, and virtual CT images 565A to 565N. The number of time instances used is for ease of explanation only.

Sub-process 330C commences at step 610 by determining a set of motion vectors (e.g., 650A) for registering each of the acquired SPECT images 645A to 645N to the acquired CT image 660 (at step 320). The registration between the CT image 660 and a SPECT image at the same time instance is not required. Therefore, the SPECT images 645A to 645N do not include the SPECT image captured at the same time instance as the CT image 660. The SPECT images 645A to 645N are compensated with geometric collimator-detector response (GCDR) without AC and SC.

Therefore, in sub-process 330C, the SPECT images 645A to 645N are the moving images and the CT image 660 is the fixed image. Each of the motion vectors 650A to 650N is a vector describing the transformation of each pixel of a SPECT image (e.g., 650A to 650N) in order to register the SPECT image (e.g., 650A to 650N) to the CT image 660. The transformation may include linear transformations (including rotation, scaling, translation, and other affine transforms) and non-rigid transformations (including radial basis functions, physical continuum models, and large deformation models). Therefore, the set of motion vectors 650A provides the transformation required to register the SPECT image 645A to the CT image 660 at a first time instance. Similarly, the set of motion vectors 650B provides the transformation required to register the SPECT image 645B to the CT image 660 at a second time instance.

Sub-process 330C proceeds from step 610 to step 620.

In step 620, the determined sets of motion vectors 650A to 650N are inversely transformed to acquire sets of inverse motion vectors 650A' to 650N'. Sub-process 330C proceeds from step 620 to step 630.

In step 630, virtual CT images 665A to 665N are generated based on the determined sets of inverse motion vectors 650A' to 650N'. To generate a virtual CT image 665A at a first time instance (which is the same time instance as SPECT image 645A), the CT image 660 is transformed using the set of inverse motion vectors 650A'. Accordingly, the respective virtual CT images 665A to 665N are generated at N time instances corresponding with the N time instances at which the SPECT images 645A to 645N are captured.

In one arrangement, the inverse motion vectors 650A' to 650N' relate to affine plus B-spline non-rigid image registration method. To perform the non-rigid registration, mutual information is normalised for 20000 pixels which are randomly selected for each resolution, and a three-level, multi-resolution approach with different grid sizes (8×8×8, 4×4×4, 1×1×1) is used to speed up both affine and B-spline registrations. For B-spline registrations, a bending energy term regularizes the deformation field to keep the rigidity and avoid the folding of local features. A stochastic gradient descent algorithm with 1000 iterations is used to iteratively solve the registration problem with adaptive step size prediction.

Therefore, by applying each set of inverse motion vectors 650A' to 650N', virtual CT images 665A to 665N are generated. Each of the virtual CT images 665A to 665N corresponds to the time instance at which the respective SPECT images 645A to 645N are captured.

Sub-process 330C concludes at the conclusion of step 630.

Assessing the Performance of SPECT/CT or PET/CT Protocol Using Virtual CT Images The SPECT/CT scans using the virtual CT images is tested using a simulation model having a population of nine, four-dimensional (4D) digital Extended Cardiac Torso (XCAT) phantoms composed of three various anatomies, i.e., body and organ sizes, and three $^{111}$In-Zevalin distributions for each anatomy. The simulation model includes respiratory and cardiac motions. Uniform distribution of activity is simulated in main organs (such as kidneys, liver, and spleen) as well as other background organs (such as muscle and other unspecified organs). Non-uniform distribution of activity is simulated in the lungs with airway activity set to zero, differing from that in lung parenchyma. The time-varying $^{111}$In distribution of each target organ is used to simulate SPECT scans acquired at 1, 12, 24, 72, and 144 hours post-injection of the radioisotope.

To simulate non-rigid organ deformations, rotations and translations for each individual organ are randomly simulated within five pixels or degrees while the volume changes are kept within 5%. The rigid body translations and rotations between each session of capturing SPECT images are randomly simulated within five pixels or degrees as well. The attenuation maps of the corresponding XCAT phantoms at different time points are generated at average energy of 192.6 keV for attenuation modelling and serve as the "real" CT (rCT) images. The virtual CT images are generated based on one rCT image at a selected time instance as described above in relation to any one of the sub-processes of FIGS. 4A to 6B.

The system 100 is simulated with a medium energy parallel-hole collimator mounted for $^{111}$In acquisition with two 14% energy windows centered at 171 and 245 keV respectively. An analytical projector modelling attenuation, scattering, and GCDR is used to generate 128 noise-free projections over 360°. In order to model the continuous nature of the activity distribution, projections are generated using XCAT phantoms with a voxel size of 0.221 cm$^3$ and then collapsed to a bin size of 0.442 cm$^3$ for reconstruction. A system calibration factor of $1.43 \times 10^4$ counts·s$^{-1}$·Bq$^{-1}$ is used to scale the noise-free projections to a clinical count level. 30-minute SPECT scans are simulated for different activities, administration and imaging time instances respectively and then modelled with Poisson noise to obtain realistic noisy projections.

Three protocols are used to assess the performance of the virtual CT images. The protocols are as follows:
  a. rCT protocol: for every time instance, both SPECT and CT images are acquired and used.
  b. 1CT protocol: only 1 CT image is acquired at the first time instance, while
  SPECT images are acquired for every time instance.
  c. vCT protocol: only 1 CT image is acquired at the first time instance, while SPECT images are acquired for every time instance. Virtual CT images are then generated at the other time instances to correspond to the generated SPECT images.

For the rCT protocol, noisy projections are reconstructed iteratively with full (AC, SC and GCDR) compensation and an ordered-subset expectation-maximization (OS-EM) algorithm of eight iterations and 16 subsets i.e., 128 updates using rCT for AC and SC. For the 1CT protocol, AC and SC are performed for SPECT images at all time instances using the acquired single CT image. For the vCT protocol, preliminary reconstruction is first performed only with GCDR correction (see FIG. 7A) to generate SPECT images for registration. A second reconstruction with full compensation is later performed after the virtual CT images are generated (see FIG. 7B).

Sub-Process 330 Optimization

For three sub-processes 330A, 330B, and 330C, the optimal time instance at which to capture the CT image of step 320 is determined. To determine the optimal time instance, a CT image is acquired at 1, 12, 24, 72 and 144 hours separately using the simulation. Virtual CT images are then generated using the respective sub-processes 330A, 330B, and 330C for each of the acquired CT image. In other words, for the CT image acquired at 1 hour using the simulation, virtual CT images are generated for the time instances of 12, 24, 72 and 144 hours. A similar operation is performed for each acquired CT image so that, for each time instance, there is a CT image and 3 virtual CT images (generated by each of the sub-processes 330A, 330B, and 330C).

At each time instance, the CT image is compared with each of the generated virtual CT images to obtain difference images and average normalized mean square errors (NMSE). The difference images and the NMSE are used to evaluate the difference between different virtual CT images and the corresponding CT image for the nine phantoms. The NMSE is determined using the equation:

$$\text{average } NMSE(x, y) = \frac{\sum_{i=1}^{4}\sum_{j=1}^{9}\sum_{k=1}^{N}(x_k - y_k)^2}{36\sum_{k=1}^{N}x_k^2},$$

where $x_k$ and $y_k$ represent the image intensity in virtual CT and rCT images, N is the number of voxels in the whole CT, j is the index for the phantoms and i is the time-point index.

As described in step 340, dosimetric analysis is performed. Organ absorbed dose error (% ODE) and normalized absolute error (% NAE) of the differential dose volume histogram (DDVH) are compared to reference OD and DVH. The % ODE and % NAE are calculated to assess the 3D dosimetric accuracy for each target organ. The results using the rCT protocol with AC and SC with no segmentation and misalignment errors served as the reference. % ODE is calculated using the equation:

$$\% \: ODE = \frac{D_{vCT,rCT,1CT} - D_{ref}}{D_{ref}} \times 100\%$$

where $D_{vCT,rCT,1CT}$ refers to the organ absorbed doses calculated based on vCT, rCT or 1CT protocols, while $D_{ref}$ refers to the reference as described above. % NAE is calculated using the equation:

$$\% \: NAE = \sum_{i=1}^{20} \frac{|V_{vCT,rCT,1CT}(i) - V_{ref}(i)|}{V_T} \times 100\%$$

For each target organ, the DDVH is calculated by computing the volume (V) in each of the 20 dose intervals (indexed by i), which are defined by the dose range divided by 20.

Figure 8A:
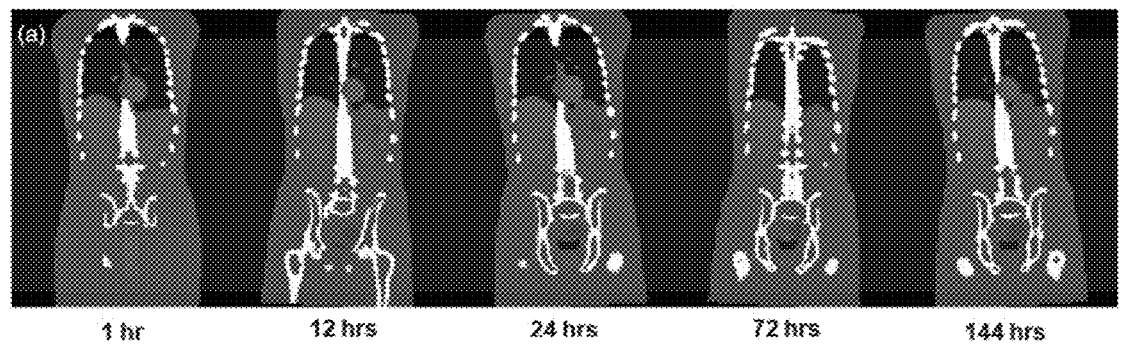
FIG. 8A shows simulated real CT images at different time instances.
Figure 8B:
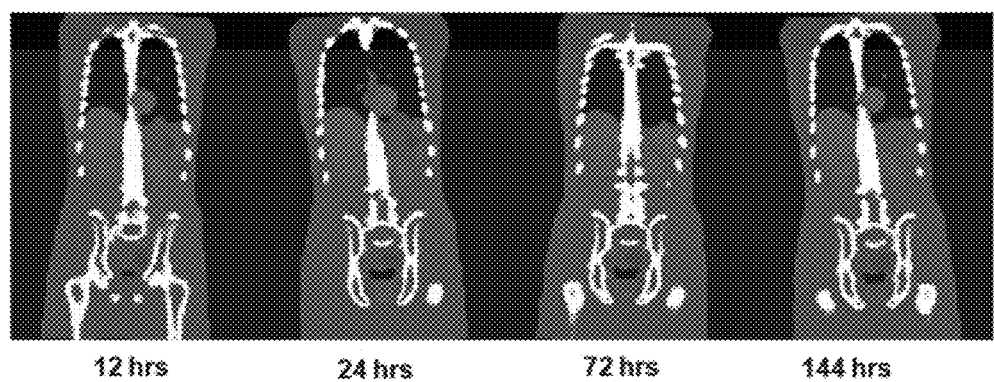
FIG. 8B shows virtual CT images generated using the sub-process of FIG. 4A.
Figure 9:
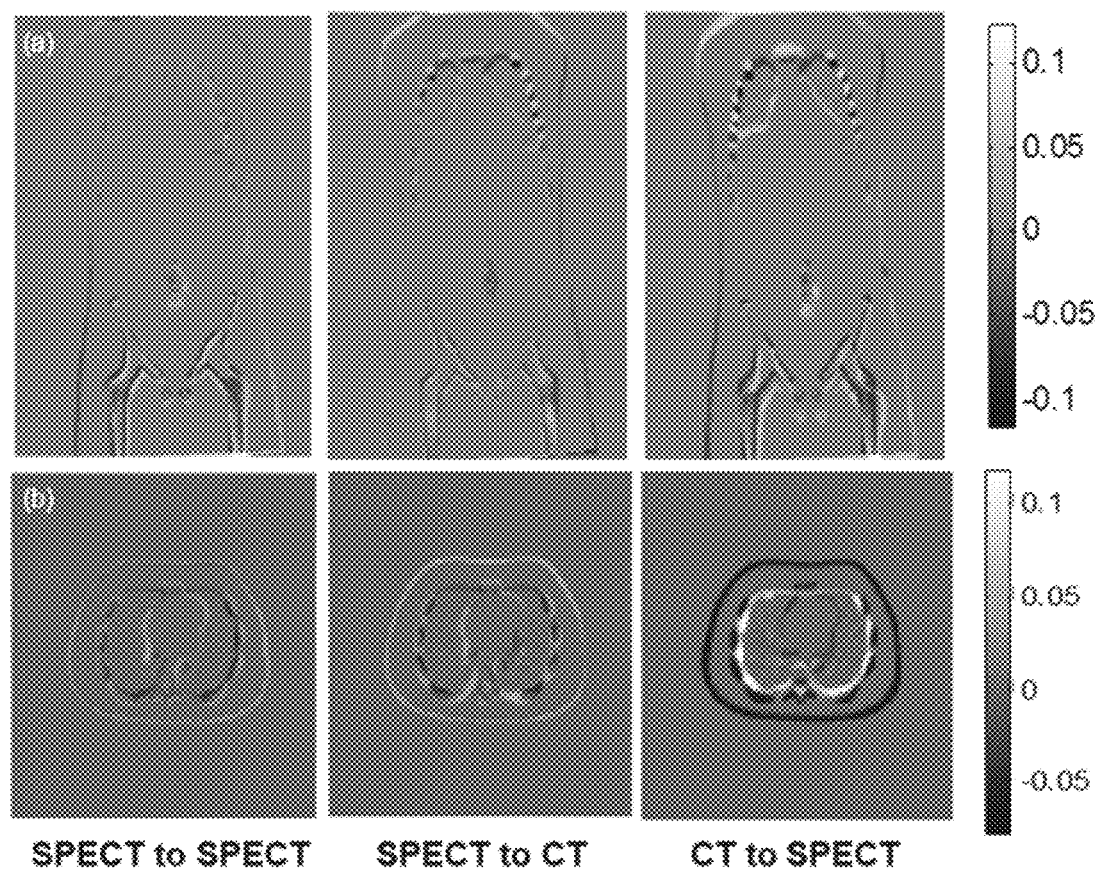
FIG. 9 shows the difference images generated when comparing simulated virtual CT images against simulated real CT images at the same time instance.

FIG. 8A shows simulated real CT images at different time instances, while FIG. 8B shows the virtual CT images generated using sub-process 330A with a single CT image (acquired at step 320) at a first time instance. FIG. 9 shows the difference images between the generated virtual CT image (generated by the respective sub-processes 330A, 330B, 330C) and the corresponding CT image for the same time instance. Errors are mostly found in bone regions such as ribs, pelvis and spine. Based on the errors, sub-process 330A shows the best result, followed by sub-process 330C and finally sub-process 330B.

Figure 10:
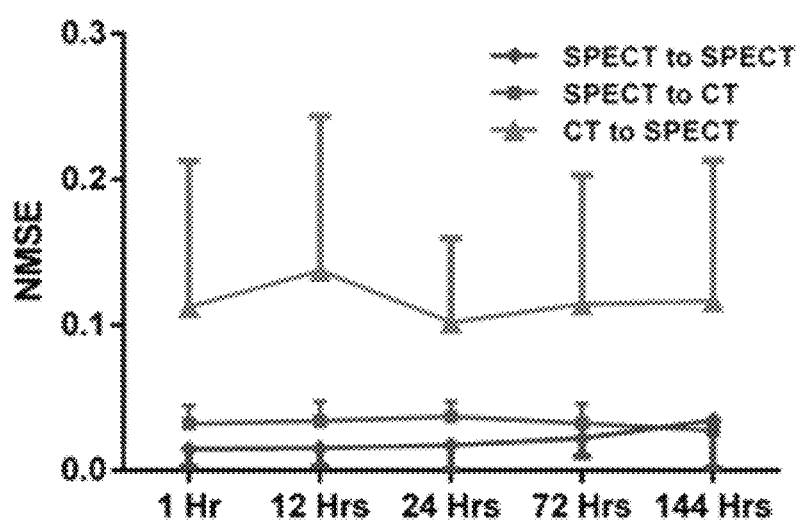
FIG. 10 shows the average normalized mean square errors (NMSE) for the virtual CT images generated by the respective sub-processes of FIGS. 4A, 5A, and 6A.

FIG. 10 shows the average NMSE results for each of the sub-processes 330A, 330B, and 330C for the nine phantoms. The error bar in FIG. 10 shows the one-side standard deviation. FIG. 10 also shows the average NMSE between the generated virtual CT images and the corresponding rCTs for all time instances, where the virtual CT images are generated using the single CT acquired at the different time instances. Similar to the result in FIG. 9, the NMSE shows that sub-process 330A provides the best result, and using the $1^{st}$ time instance as the moving image shows the best results.

Dosimetric Results Evaluation

As described above, sub-process 330A provides the best result for the vCT protocol. The dosimetric results of vCT protocol (generated using sub-process 330A) are compared against the rCT and 1CT protocols. For vCT and rCT protocols, the target organs (i.e., liver, spleen, kidneys and lungs) are semi-automatically segmented at all time instances on respective virtual CT and real CT images. Organ-by-organ non-rigid registration are then applied.

For the 1CT protocol, as some organ-of-interest regions cannot be delineated from SPECT images at later time instances, whole body SPECT registration is performed while the single CT image is used for organ segmentation. Voxel-by-voxel trapezoidal integration is performed on aligned images over five time points and up to 1000 hours post-injection, assuming only physical decay after the last time point to obtain the cumulative activity, followed by Y-90 voxel S-value kernel (VSK)[22] convolution to generate the 3D dose distribution.

Figure 11A:
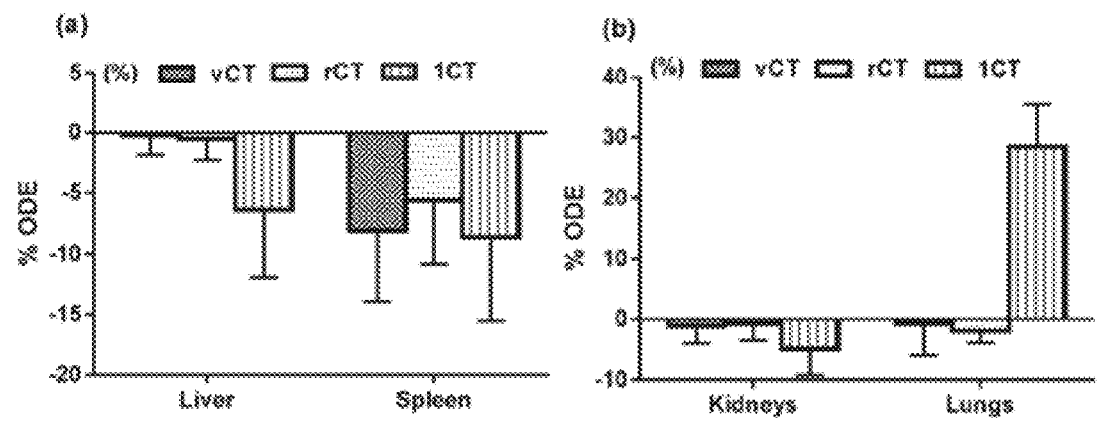
FIGS. 11A and 11B show the dosimetric results in assessing the performance of using the virtual CT images.
Figure 11B:
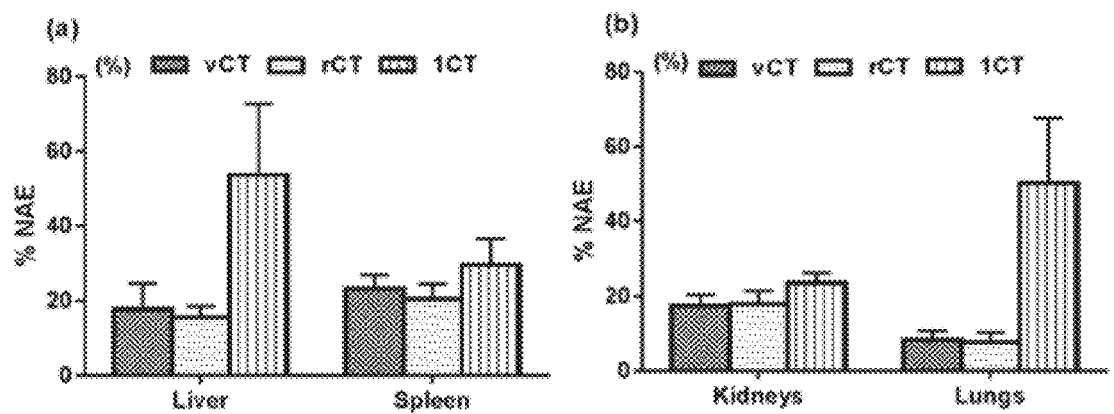

Sub-process 330A with a single CT image at the first time instance is further evaluated. FIGS. 11A and 11B show the dosimetric results of vCT, rCT and 1CT protocols for liver, spleen, kidneys and lungs. For the vCT protocol, both % ODE and % NAE are smaller compared to 1CT protocol for all organs and approached those of rCT protocol. For example, the % ODEs for the liver are −0.24±1.56% vs. −0.49±1.76% vs. −6.37±5.63% for vCT, rCT and 1CT protocols respectively, while the % ODEs are −1.05±2.89% vs. −0.69±2.74% vs. −4.87±4.35% for kidneys. The % ODE decreases in magnitude from about 28% to about −1% using vCT protocol in comparison with 1CT protocol for lungs i.e., −0.73±5.15% vs. 28.46±6.99%. For all organs, the vCT protocol's DDVH also approach those of rCT protocol and show improvement when compared against 1CT protocol i.e., 17.79±6.82% vs. 15.60±2.96% vs. 53.54±18.99% for the liver, and 23.33±3.56% vs. 20.48±4.03% vs. 29.56±7.04% for the spleen respectively.

Figure 7A:
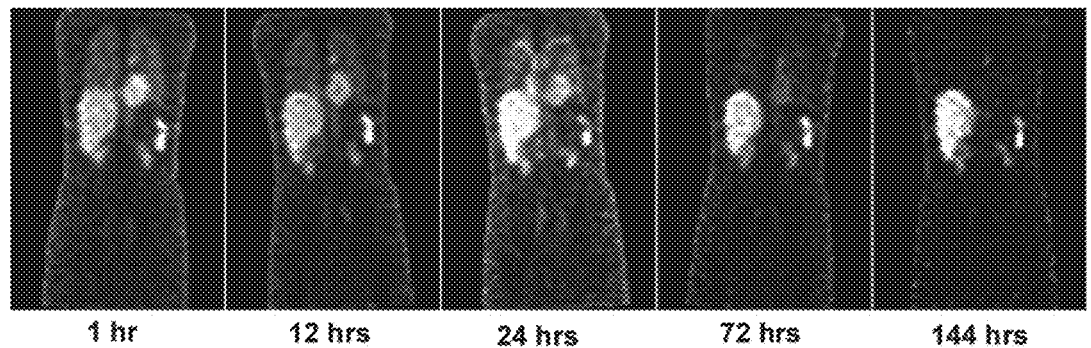
FIG. 7A shows SPECT images generated by a model for registration (without attenuation and scatter correction)
Figure 7B:
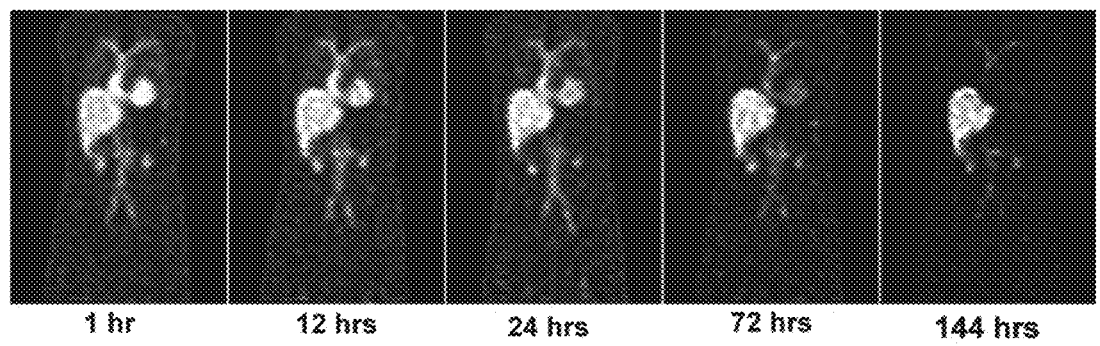
FIG. 7B shows the SPECT images of FIG. 7A after attenuation and scatter correction using the generated virtual CT images.

Comparing FIG. 7A and FIG. 7B, it can be observed that the lung and bone regions are more prominent in the preliminary reconstructed images without AC and SC, due to the fact that bone has higher attenuation coefficients and the lungs have lower attenuation coefficients than soft tissues. The non-attenuation corrected images are beneficial for registration, especially for sub-process 330A where the edges of both moving and fixed images are enhanced. Further, image registration for a single modality is generally less challenging than dual-modality, thereby resulting in sub-process 330A being preferred. The common use of gradient descent based optimization algorithms in image registration to compute the derivative of the moving image also favours choosing the image with lower noise, i.e., the first time instance image as the moving image for non-rigid registration.

For dual-modality image registration, if there is more structural information in the moving images than in the fixed image, the registration process tends to maximize the similarity by "shrinking" the additional structures in the moving images (the bottom images of FIG. 9). Thus, in order to avoid erroneous registration, it is suggested that images with more structural details be used as the fixed images i.e., sub-process 330C instead of sub-process 330B for virtual CT image generation. Additionally, cubic B-spline interpolation is applied in all registrations, which provides a realistic, continuous nature of the distribution. It does however, tend to reduce high frequency components and is limited on organ edge performance as shown in FIGS. 8A and 8B.

The virtual CT images could be used for AC and SC to provide more accurate quantitative reconstruction and furthermore, it could be used to aid image registration and organ segmentation especially for organs with low uptake on SPECT images. Furthermore, the virtual CT images enhance the dosimetric accuracy as compared to the conventional 1CT protocol without increasing the patient radiation dose i.e., still about 19 mSv. It should be recognized that the radiation dose from the CT scan used for treatment planning is much lower than that of the diagnostic CTs, let alone the subsequent TRT.

Therefore, the method 300 and sub-processes 330A, 330B, 330C lower the radiation dose from the CT scan, to the benefit of the patient.

INDUSTRIAL APPLICABILITY

The arrangements described are applicable to the computer and data processing industries and particularly for dosimetric analysis of organs.

The foregoing describes only some embodiments of the present invention, and modifications and/or changes can be made thereto without departing from the scope and spirit of the invention, the embodiments being illustrative and not restrictive.

The invention claimed is:

1. A system comprising:
a SPECT device;
a CT device; and
a computer comprising memory and a processor in communication with the memory, the memory comprising a computer application program for performing dosimetric analysis of an organ, wherein the dosimetric analysis of the organ comprising:
receiving single photon emission computed tomography (SPECT) images at time instances, the SPECT images relating to the organ and being preliminarily reconstructed without attenuation and scatter corrections;
receiving a computed tomography (CT) image at a first time instance, the received CT image relating to the organ;
generating virtual CT images at the other time instances based on the received SPECT images and the received CT image;
reconstructing the received SPECT images with attenuation and scatter corrections based on the received CT image;
mapping out the organ on the reconstructed SPECT images after organ segmentation on the received CT image and the generated virtual CT images; and
measuring an absorbed dose of ionising radiation on the organ based on the reconstructed SPECT images, the received CT image, and the generated virtual CT images,
wherein segmented images obtained from said organ segmentation are curve fitted to estimate cumulated activity of the ionising radiation, followed by voxel S-value kernel convolution to calculate the absorbed dose of the organ.

2. The system of claim 1, wherein the generating virtual CT images comprises:
determining a set of motion vectors for registering the received CT image to each of the received SPECT images at the other time instances; and
generating the virtual CT images at the other time instances by applying the determined sets of motion vectors to the received CT image.

3. The system of claim 1, wherein the generating virtual CT images comprises:
determining a set of motion vectors for registering each of the received SPECT images to the received CT image at the other time instances;
inverse transforming the sets of motion vectors; and
generating the virtual CT images at the other time instances by applying the inverse transformed sets of motion vectors to the received CT image.

4. The system of claim 1, wherein the generating virtual CT images comprises:
determining one of the SPECT images corresponding to the received CT image;
determining a set of motion vectors for registering the determined SPECT image to each of the remaining SPECT images at the other time instances; and
generating the virtual CT images at the other time instances by applying the determined sets of motion vectors to the received CT image.

5. The system of claim 4, wherein the determined SPECT image is acquired at the same time instance as the received CT image.

6. A non-transitory computer readable medium comprising a computer application program for performing dosimetric analysis of an organ, the dosimetric analysis of the organ comprising:
receiving single photon emission computed tomography (SPECT) images at time instances, the SPECT images relating to the organ and being preliminarily reconstructed without attenuation and scatter corrections;
receiving a computed tomography (CT) image at a first time instance, the received CT image relating to the organ;
generating virtual CT images at the other time instances based on the received SPECT images and the received CT image;
reconstructing the received SPECT images with attenuation and scatter corrections based on the received CT image;
mapping out the organ on the reconstructed SPECT images after organ segmentation on the received CT image and the generated virtual CT images; and
measuring an absorbed dose of ionising radiation on the organ based on the reconstructed SPECT images, the received CT image, and the generated virtual CT images,
wherein segmented images obtained from said organ segmentation are curve fitted to estimate cumulated activity of the ionising radiation, followed by voxel S-value kernel convolution to calculate the absorbed dose of the organ.

7. The non-transitory computer readable medium of claim 6, wherein the generating virtual CT images comprises:
determining a set of motion vectors for registering the received CT image to each of the received SPECT images at the other time instances; and generating the virtual CT images at the other time instances by applying the determined sets of motion vectors to the received CT image.

8. The non-transitory computer readable medium of claim 6, wherein the generating of virtual CT images comprises:
determining a set of motion vectors for registering each of the received SPECT images to the received CT image at the other time instances;
inverse transforming the sets of motion vectors; and
generating the virtual CT images at the other time instances by applying the inverse transformed sets of motion vectors to the received CT image.

9. The non-transitory computer readable medium of claim 6, wherein the generating virtual CT images comprises:
determining one of the SPECT images corresponding to the received CT image;
determining a set of motion vectors for registering the determined SPECT image to each of the remaining SPECT images at the other time instances; and
generating the virtual CT images at the other time instances by applying the determined sets of motion vectors to the received CT image.

10. The non-transitory computer readable medium of claim 9, wherein the determined SPECT image is acquired at the same time instance as the received CT image.

11. A computer-implemented method of performing dosimetric analysis, the method comprising:
receiving single photon emission computed tomography (SPECT) images at time instances, the SPECT images relating to an organ and being preliminarily reconstructed without attenuation and scatter corrections;
receiving a computed tomography (CT) image at a first time instance, the received CT image relating to the organ;
generating virtual CT images at the other time instances based on the received SPECT images and the received CT image;
reconstructing the received SPECT images with attenuation and scatter corrections based on the received CT image;
mapping out the organ on the reconstructed SPECT images after organ segmentation on the received CT image and the generated virtual CT images; and
measuring an absorbed dose of ionising radiation on the organ based on the reconstructed SPECT images, the received CT image, and the generated virtual CT images,
wherein segmented images obtained from said organ segmentation are curve fitted to estimate cumulated activity of the ionising radiation, followed by voxel S-value kernel convolution to calculate the absorbed dose of the organ.

12. The computer-implemented method of claim 11, wherein the generating virtual CT images comprises:
determining a set of motion vectors for registering the received CT image to each of the received SPECT images at the other time instances; and
generating the virtual CT images at the other time instances by applying the determined sets of motion vectors to the received CT image.

13. The computer-implemented method of claim 11, wherein the generating virtual CT images comprises:
determining a set of motion vectors for registering each of the received SPECT images to the received CT image at the other time instances;
inverse transforming the sets of motion vectors; and
generating the virtual CT images at the other time instances by applying the inverse transformed sets of motion vectors to the received CT image.

14. The computer-implemented method of claim 11, wherein the generating virtual CT images comprises:
determining one of the SPECT images corresponding to the received CT image;
determining a set of motion vectors for registering the determined SPECT image to each of the remaining SPECT images at the other time instances; and
generating the virtual CT images at the other time instances by applying the determined sets of motion vectors to the received CT image.

15. The computer-implemented method of claim 14, wherein the determined SPECT image is acquired at the same time instance as the received CT image.

* * * * *